United States Patent [19]

Malfitano

[11] Patent Number: 4,666,440
[45] Date of Patent: May 19, 1987

[54] SPINED SANITARY NAPKIN AND BELT

[76] Inventor: Amanda Malfitano, 161 - 77th St., Brooklyn, N.Y. 11209

[21] Appl. No.: 303,762

[22] Filed: Sep. 21, 1981

Related U.S. Application Data

[63] Continuation-in-part of Ser. No. 46,681, Jul. 30, 1979, abandoned.

[51] Int. Cl.⁴ ............................................. A61F 13/16
[52] U.S. Cl. .................... 604/391; 604/385 R
[58] Field of Search ................. 128/289, 290 R, 291; 604/391–392, 358, 385, 386, 394, 395, 397, 400–402

[56] References Cited

U.S. PATENT DOCUMENTS

| | | |
|---|---|---|
| 2,747,575 | 5/1956 | Mercer ................................ 604/385 |
| 2,764,158 | 9/1956 | Thornton ............................ 604/394 |
| 3,057,354 | 10/1962 | Roberts et al. ...................... 604/400 |
| 3,092,104 | 6/1963 | Mosier ................................. 604/397 |
| 3,375,826 | 4/1968 | Field ................................... 604/402 |

Primary Examiner—C. Fred Rosenbaum
Assistant Examiner—Sherri E. Vinyard

[57] ABSTRACT

A sanitary napkin assembly for feminine hygiene comprising an elastic belt forming a waistband having fasteners at each end for securement about the waist of the wearer. Fabric tabs depend from one end of the belt and from the middle thereof to which "Velcro" strips are attached. A sanitary napkin having a spine of "Velcro" strips attached thereto is secured in a conveniently adjustable manner to the depending tabs, the spine serving to reinforce the sanitary napkin and hold a central protrusion against the wearer.

3 Claims, 4 Drawing Figures

SPINED SANITARY NAPKIN AND BELT

REFERENCE TO RELATED APPLICATIONS

This application is a continuation in part of the application of Amanda Malfitano, Ser. No. 046,681 7/30/79 now abandoned for Sanitary Napkin Assembly.

BACKGROUND OF THE INVENTION

1. Field of the Invention

This invention relates to the class of medicinal appliances and more particularly to a spined sanitary napkin and belt therefore.

2. Description of the Prior Art

Various types of sanitary napkins are now being sold employing a waistband to which absorbent pads are secured by various types of plastic or metal fasteners or by safety pins. These sanitary napkins are sold under the various trademarks "Kotex", "Modess", and other well-known such products have been used in the past all employing mechanical fastener means or even safety pins for securement. These metal or plastic fasteners are often unwieldly or difficult to adjust and may cause discomfort and possible injury to the wearer, as well as creating unsightly bulges.

In U.S. Pat. No. 3,095,879 there is disclosed a sanitary napkin belt using mechanical fasteners not employing "Velcro" and showing no central spine for the sanitary napkin.

U.S. Pat. No. 4,022,212 discloses a panty with a detachable crotch portion for use as a sanitary napkin and using "Velcro" fasteners. No central spine is disclosed nor is a protrusion employed.

Various types of tampons for insertion in vaginal orifices have been widely used but have lately come into disfavor because they have become widely suspect of causing infection and serious fevers clearly associated with their use. However, the tampon has given many wearers confidence and assurance of protection because of intimate contact. The present invention provides similar feelings of assurance by providing more intimate contact while avoiding the medical disadvantages of the tampon.

SUMMARY OF THE INVENTION

The present invention overcomes the disadvantages of the prior art sanitary napkin assemblies by utilizing the well-known hook-like filament material sold under the trademark "Velcro" for attaching the sanitary napkin to the supporting belt. It is the concept of the present invention to sew "Velcro" strips to a pair of tabs one depending from an end of the belt and the other from the middle thereof. Complementary strips of "Velcro" material are secured to the spine of an absorbent pad. The spine is centrally disposed with respect to the absorbent pad and of relatively more rigid material. The spine may be made out of "Velcro" material throughout for convenience of use and manufacture and the absorbent pad may be then pressed into engagement with the "Velcro" strips on the belt for secure attachment yet permitting a wide range of adjustability and no unsightly bulges or possibility of discomfort, while the spine comfortably presses the protrusion against the genital area of the wearer providing the assurance of protection so desired by the wearer.

DETAILED DESCRIPTION OF THE INVENTION

Figure 1:
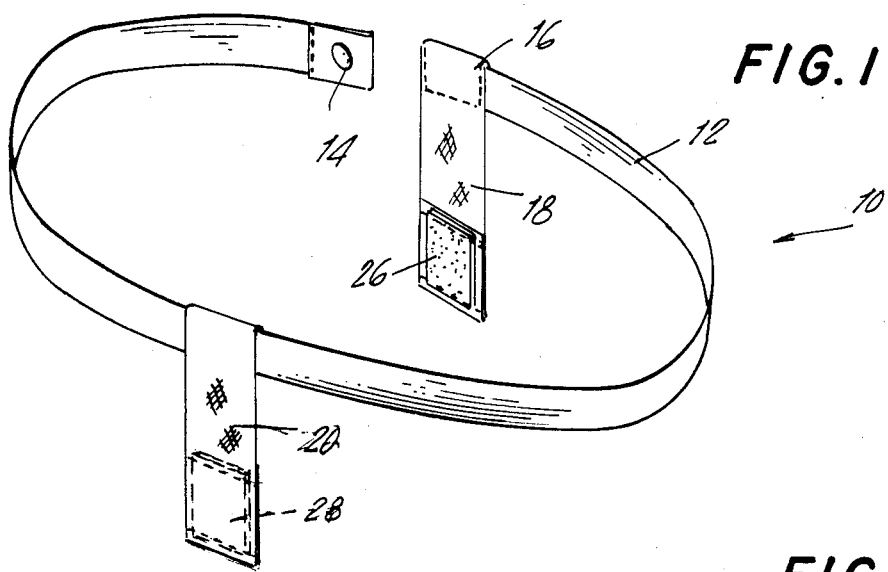
FIG. 1 is a perspective view of a belt constructed in accordance with the concepts of the present invention.
Figure 4:
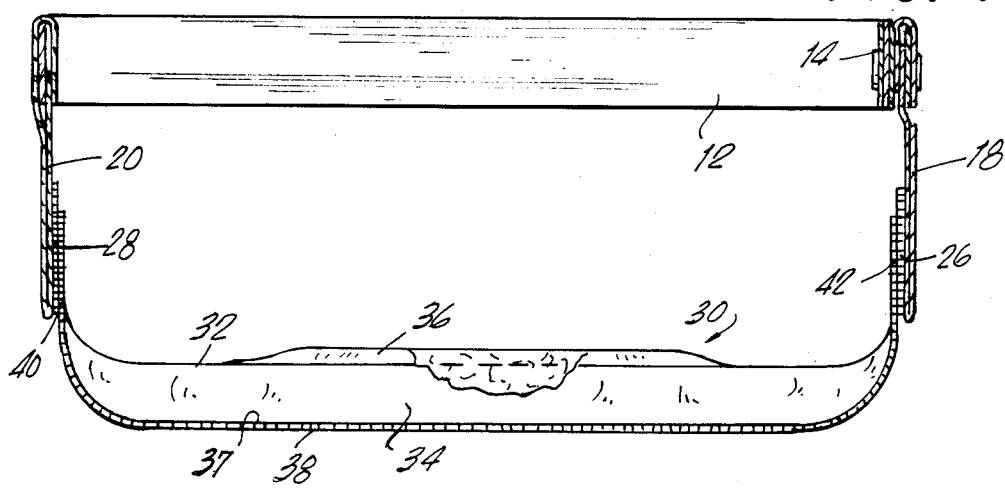
FIG. 4 is a sectional detail view illustrating the belt and napkin in an assembled condition.
Figure 2:
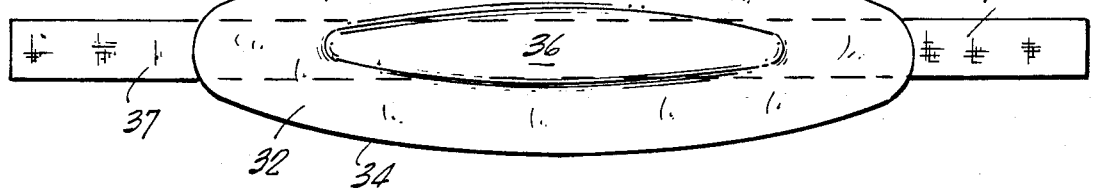
FIG. 2 is a top plan view of a sanitary napkin employing the present invention.
Figure 3:
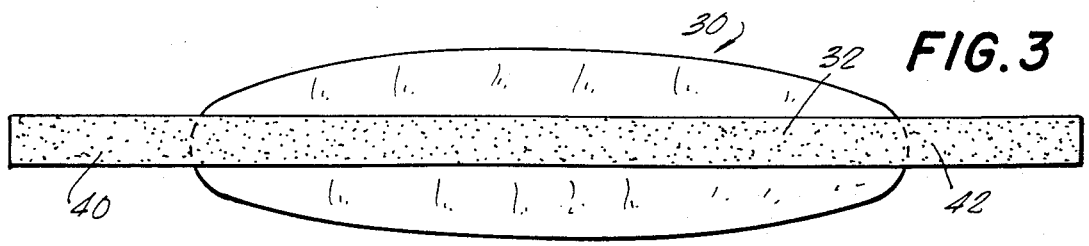
FIG. 3 is a bottom plan view of the sanitary napkin.

With continuing reference to the accompanying drawing, wherein like reference numerals designate similar parts throughout the various views, reference numeral 10 generally designates a belt formed of elastic band 12 adapted to fit around the waist of the wearer and including complementary "Velcro"-type fasteners 14 and 16 at the opposite ends thereof for adjustable and comfortable attachment about the waist of a wearer. Depending from one end of the band 12 is a tab 18 of fabric material and a tab 20 is sewn to and depends from the center of the band 12. Strips 22 and 24 of "Velcro" which is a hook-like filament material, sold under the trade name "Velcro", are sewn as at 26 and 28, to the fabric material of the tabs 18 and 20. The use of sewing means attaching the "Velcro" strips 22 and 24 to the tabs is desirable due to the fact that the waist band may be easily washed and reused without the possibility of a bond between the strips and the tabs being broken during washing or drying operations thereon. Alternatively the tabs may be made completely of "Velcro" material providing for an even wider range of adjustability.

A sanitary napkin generally indicated at 30 contains an absorbent pad portion 32 and a fabric wrapper 34. The pad 32 has an oval, ogive or diamond shaped protuberance 36 conforming generally to the inner conformation of the genital area of the wearer and designed to fit therein and be pressed therein by a spine 38 of material more rigid than the pad 32 or wrapper 34 to which the spine is attached. The spine 38 is centrally disposed with respect to the pad 32 and much less wide so as to underlie protuberance 36 and urge the protrusion inwardly with respect to the wearer while allowing the balance of the pad to bend as necessary outwardly to comfortably accommodate the thigh portions of the wearer. The spine 36 is perferably formed entirely of "Velcro" material facing downwardly away from the protuberance 36 for more effective attachment to the tabs 26 and 28 with a complete range of adjustability with the tabs underlying the spine 38 to urge the spine to direct the protuberance 36 into position. Alternatively, "Velcro" strips 40 and 42 are sewn as at 44 and 46 to the spine 38.

In use, the belt 10 is positioned about the body of the wearer with the "Velcro" fasteners adjustably secured at the center of the waist of the user so that the tabs 18 and 20 depend at the front and back of the wearer. The sanitary napkin 30 is disposed between the legs of the wearer and the "Velcro" spine 38 or tabs 40 and 42 may be simply engaged and adjusted with the "Velcro" strips 26 and 28 by simple adjustable pressing of the complementary "Velcro" material together. This allows for a wide and complete range of adjustment without having to engage hooks, safety pins, or like fasteners.

What is claimed is:

1. A sanitary napkin assembly for feminine hygiene comprising an elastic waistband having fastening means at each end for securement about the waist of the wearer, a fabric tab depending from one end of said band and from the middle of said band so that when the ends of said band are fastened so that said ends overlie the middle of the wearer's waist, said tabs depend in front and back of the wearer, first strips of hook-like filament material on said tabs facing inwardly toward the wearer, an absorbent napkin including an absorbent pad and having an upper protuberance conforming to the shape of the genital area of the wearer and adapted to penetrate into said area, said absorbent napkin including a centrally disposed spine more rigid than said pad having hook-like filament material facing downward along the entire length thereof complementary to said first strips and adhering thereto so that said napkin is supported between the legs of the wearer with said protuberance urged by said spine and the connection with said tabs to penetrate the genital area of the wearer.

2. A sanitary napkin assembly according to claim 1, wherein said first strips are sewn to said tabs.

3. A sanitary napkin assembly according to claim 1, wherein said spine is of less width than said absorbent pad, said protuberance being of oval, ogive or diamond shape.

* * * * *